United States Patent [19]

Jacquet et al.

[11] 4,390,522

[45] Jun. 28, 1983

[54] COSMETIC AGENTS BASED ON CATIONIC POLYMERS, COSMETIC COMPOSITIONS CONTAINING THE SAME AND THE USE OF SAID COSMETIC AGENTS

[75] Inventors: Bernard Jacquet, Antony; Gerard Lang, Epinay-sur-Seine; Alain Malaval, Aulnay sous Bois; Serge Forestier, Claye Souilly; Do Le Trung, Drancy, all of France

[73] Assignee: Societe Anonyme dite: L'Oreal, Paris, France

[21] Appl. No.: 217,401

[22] Filed: Dec. 17, 1980

[30] Foreign Application Priority Data

Dec. 21, 1979 [FR] France ................. 79 31429

[51] Int. Cl.$^3$ ............ A61K 7/00; A61K 7/04; A61K 7/06; A61K 7/09
[52] U.S. Cl. ..................... 424/45; 424/70; 424/71; 424/61; 424/DIG. 1; 424/DIG. 2
[58] Field of Search ............ 424/70, 71, 61, DIG. 1, 424/DIG. 2

[56] References Cited

U.S. PATENT DOCUMENTS 4,110,263  8/1978  Lindemann et al. .................. 424/70
4,150,115  4/1979  Jacquet et al. .............. 424/DIG. 1
4,217,914  8/1980  Jacquet et al. ......................... 424/72

FOREIGN PATENT DOCUMENTS 1508215  5/1975  United Kingdom .
2000168  1/1979  United Kingdom .

*Primary Examiner*—Delbert R. Phillips
*Assistant Examiner*—F. T. Moezie
*Attorney, Agent, or Firm*—Cushman, Darby & Cushman

[57] ABSTRACT

A cosmetic composition for application to the hair, skin or nails comprises in a cosmetic vehicle selected from water, a lower alkanol or a dilute lower alkanol solution, 0.01 to 15 percent by weight of a cationic polymer having units of the formula

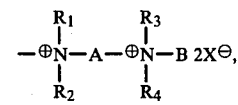

said polymer having a molecular weight between 1,000 and 50,000. $R_1$, $R_2$, $R_3$ and $R_4$ each independently represent alkyl or hydroxyalkyl wherein the alkyl of each has 1-20 carbon atoms. A is alkylene, hydroxyalkylene, $-(CH_2)_n-Z-(CH_2)_n-$ wherein Z is oxygen and n is a whole number ranging from 2-10, or $-EO)_{m1}(DO_m D_1$ wherein E is alkylene or hydroxyalkylene containing 1-5 carbon atoms, $m_1$ is 0 or 1, m is 1-600 with the proviso that m is greater than 1 when $m_1=0$. $D_1$ represents E when $m_1=1$ and $D_1$ represents D when $m_1=0$. B represents $-EO)_{m1} (DO)_m D_1$ wherein E, D, $D_1$, m and $m_1$ are defined above $X^\ominus$ represents a halide anion.

36 Claims, No Drawings

COSMETIC AGENTS BASED ON CATIONIC POLYMERS, COSMETIC COMPOSITIONS CONTAINING THE SAME AND THE USE OF SAID COSMETIC AGENTS

This invention relates to cationic polymers for use as cosmetic agents, to cosmetic compositions containing these polymers, and to a process for treating the hair, skin and nails with said polymers.

It has already been proposed to use various cationic polymers as pesticides, flocculants, etc. It has also been proposed to use certain cationic polymers as cosmetic agents; see, for example, French Pat. No. 75.15162.

It has now been discovered that the use of certain particular cationic polymers offers advantages relative to cationic polymers previously used. Some of these advantages will be set forth in the following specification.

The invention relates to cationic polymers for use, as cosmetic agents, of said polymers containing units of the formula (I):

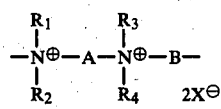

wherein:

$R_1$, $R_2$, $R_3$, $R_4$ independently represent a hydrocarbon group, optionally substituted, or the pairs $R_1$, $R_2$ and/or $R_3$, $R_4$ represent, together with the nitrogen atom to which they are attached, a heterocycle that can also contain, one or more other heteroatoms.

or the pairs $R_1$, $R_3$ and/or $R_2$, $R_4$ together form a bivalent group linking the two nitrogen atoms represented in the unit of formula (I), or the pairs $R_1$, $R_3$ and/or $R_2$, $R_4$ form with A a cyclic group such as one having the formula

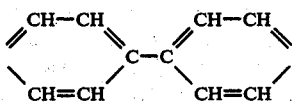

wherein

A is linear or branched alkylene, hydroxyalkylene or alkenylene, o-, m- or p-xylylene,:

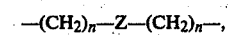

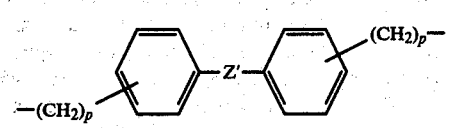

or

wherein p is a whole number varying from 0 to 2,

Z' is an oxygen atom, —CO—, —CHOH—, —SO$_2$— or alkylene having 1 to 4 carbon atoms n is a whole number varying from 2 to 10, Z represents —O—, —S—, —SO—, —SO$_2$—, —S—S,

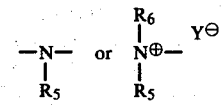

wherein $R_5$ is hydrogen or an aliphatic, alicyclic, aryl or arylaliphatic group having 20 atoms at most, $R_6$ is an aliphatic or arylaliphatic group containing 20 carbon atoms at most, or $R_6$ is a bivalent group constituting a bridge for cross-linking with similar groups of another macromolecular chain, E represents alkylene or hydroalkylene containing 1 to 10 carbon atoms, D represents a bivalent hydrocarbon group containing 1 to 5 carbon atoms, $m_1$ represents a number equal to 0 or 1, m represents a number from 1 to 600 with the proviso that m is greater than 1 when $m_1=0$, $D_1$ represents E when $m_1=1$, and $D_1$ represents D when $m_1=0$, B represents a group of the formula:

$$-EO)_{m_1}(DO)_m D_1-$$

wherein

E, D, $D_1$, m and $m_1$ are defined as above, and $X^\ominus$ and $Y^\ominus$ represent an anion.

To simplify polymers whose recurrent groups have formula (I), they will be designated below by the expression "polymers of formula (I)."

The end groups of the polymers of formula (I) vary with the starting reagents and their proportions. They can particularly be of the type $$\begin{matrix} R_1 \\ \diagdown \\ R_2 \diagup \end{matrix} N-A- \quad \text{or} \quad \begin{matrix} R_3 \\ \diagdown \\ R_4 \diagup \end{matrix} N-A-$$

or of the X—B— type.

In the polymers of formula (I), $X^\ominus$ and $Y^\ominus$ particularly represent a halide anion (bromide, iodide or chloride) or an anion derived from other inorganic acids such as phosphoric acid or sulfuric acid, etc . . . , or again an anion derived from an organic, sulfonic or carboxylic acid, particularly an alkanoic acid having 2 to 12 carbon atoms (for example, acetic acid), benzoic acid, lactic acid, citric acid, or paratoluene-sulfonic acid; substituents $R_1$, $R_2$, $R_3$ and $R_4$ particularly represent a substituted or unsubstituted aliphatic, alicyclic or arylaliphatic group containing 20 carbon atoms at most; for example, $R_1$ and $R_3$ represent an alkyl or hydroalkyl group having 1 to 6 carbon atoms, and $R_2$ and $R_4$ represent an alkyl, hydroalkyl or cycloalkylalkyl group having less than 20 carbon atoms and preferably having not more than 16 carbon atoms, a cycloalkyl group with 5 or 6 chains, an aralkyl group such as a phenylalkyl group whose alkyl moiety preferably comprises from 1 to 3 carbon atoms; when the pairs $R_1$, $R_2$ or $R_3$, $R_4$, attached to the same nitrogen atom, constitute a ring with it, they can together represent particularly a polymethylene radical having 2 to 6 carbon atoms, and the ring can further include an oxygen heteroatom; when the pairs $R_1$, $R_3$ or $R_2$, $R_4$ together form a bivalent group, they constitute particularly a hydrocarbon group having 2 to 4 carbon atoms, and in particular an alkylene group having two carbon atoms; A particularly represents an alkylene group of the formula:

$$-(CH_2)_y-CH(K_1)-(CH_2)_x-CH(K_2)-(CH_2)_t-$$

wherein
x, y and t are whole numbers that can vary from 0 to 11, so that the total (x+y+t) is greater than or equal to 0 and less than 18, and $K_1$ and $K_2$ represent a hydrogen atom or an aliphatic group having less than 18 carbon atoms; when $K_1$ or $K_2$ is an aliphatic group, it constitutes particularly an alkyl group having 1 to 17 carbon atoms, and preferably 1 to 12 carbon atoms; x, y and t are preferably numbers that can vary from 0 to 5; or else A represents an alkenyl group of the formula $$-(CH_2)_v-CH=CH-(CH_2)_u-,$$

wherein
—v and u are whole numbers so that the total (v+u) is 2 to 18, and preferably 2 to 10; D particularly represents a linear or branched alkylene group having 2 to 4 carbon atoms; E particularly represents a group $$-CH_2-CHOH-CH_2- \text{ or } -(CH_2)_3-;$$

when $R_5$ or $R_6$ is an aliphatic group, it constitutes particularly an alkyl or cycloalkylaryl group having at most 20 carbon atoms and preferably 1 to 16 carbon atoms; when $R_5$ represents an alicyclic group, there is involved particularly a cycloalkyl group with 5 to 6 chains; when $R_5$ or $R_6$ represents an arylaliphatic group such as a phenylalkyl group the alkyl moiety preferably comprises 1 to 3 carbon atoms, and $R_5$ or $R_6$ represents in particular benzyl; when $R_6$ represents a bivalent group constituting a crosslinking bridge, it constitutes particularly a polymethylene group having, for example, 3 to 10 carbon atoms, a xylylene (ortho, meta or para) group, a group of the formula $$-(CH_2)_n-O-(CH_2)_n-,$$

wherein
n is defined above, a group of the formula $$-CH_2-CHOH-CH_2-,$$

or
a group of the formula $$-(EO)_{m_1}(D-0)_m-D_1-,$$

wherein
E, D, $D_1$, m and $m_1$ are defined above, etc.

Of the polymers of formula (I) for use as cosmetic agents according to the invention, there will be cited particularly those for which $R_1$ and $R_3$ are methyl, ethyl or hydroxyethyl; $R_2$ and $R_4$ are alkyl or hydroxyalkyl groups having 1 to 10 carbon atoms, benzyl or cyclohexyl groups; or $R_1$ and $R_3$, or $R_2$ and $R_4$ together represent $$-(CH_2)_5- \text{ or } -(CH_2)_2-O-(CH_2)_2-;$$

A is a xylylene group, a polymethylene group having 2 to 12 carbon atoms optionally branched by one or two alkyl substituents having 1 to 12 carbon atoms; n is equal to 2 or 3; m is a number varying from 2 to 18; $X^\ominus$ represent a halide anion, particularly iodide, chloride or bromide; $Y^\ominus$ is a halide anion (iodide, bromide or chloride) or a bisulfate $HSO_4^\ominus$ or methosulfate $CH_3SO_4^\ominus$ anion.

It should be noted that the invention extends to the cosmetic use of polymers of formula (I) in which the groups A, B, $R_1$, $R_2$, $R_3$ and/or $R_4$ have many different values in the same polymer I.

The polymers of formula (I) can be prepared by a standard process consisting of polycondensing a ditertiary diamine of the formula:

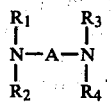

wherein:
A, $R_1$, $R_2$, $R_3$ and $R_4$ are defined above, with a compound of the formula X—B—X, wherein X and B are defined above.

For example, the polycondensation reaction is performed in a solvent or mixture of solvents favoring quaternization reactions, such as water, dimethylformamdide, acetonitrile, lower alcohols, particularly, lower alkanols such as methanol, etc.

The reaction temperature can vary between 10° and 150° C. and preferably between 20° and 100° C.

The reaction time depends on the nature of the solvents, the starting reagents and the desired degree of polymerization.

Generally the starting reagents are reacted in equimolecular quantities but it is possible to use either the diamine or the dihalide in slight excess, this excess being less than 20 moles percent.

The resulting polycondensate is optionally isolated at the end of the reaction by filtering or by concentrating the reaction mixture.

It is possible to regulate the average length of the chains by adding at the beginning of or during the reaction a slight amount (1 to 15 mole percent relative to one of the reagents) of a monofunctional reagent such as a tertiary amine or a monohalide. In this case, at least a part of the end groups of the polymer of formula I obtained is made up either of the tertiary amine group used or the hydrocarbon group of the monohalide.

The invention includes the cosmetic use of polymers of formula (I) having such end groups.

Instead of the starting reagent it is also possible to use either a mixture of ditertiary diamines or a mixture of dihalides or again a mixture of ditertiary amines and a mixture of dihalides, provided the ratio of the total molar amounts of diamines and dihalides is close to 1.

The starting products of formula $B(X)_2$ can be prepared according to standard processes such as those described, for example, in French patent application No. 76.02948; by Perry Hibbert, Canad. J. Res. (B) 14, (1936) 82; Fordyce and Lowell H., J. Am Chem. Soc., 61 (1939), 190; or Johansson, Eur. J. Biochem., 33, 379 (1973).

The starting ditertiary diamines can be prepared by standard processes described, for example, in French Pat. No. 75.15162; and in U.S. Pat. No. 4,110,263.

When A represents $-(CH_2)_n-Z-(CH_2)_n-$, wherein Z=—N($R_5$)-. The tertiary nitrogen of the Z group can be quaternized, totally or partially, by an additional stage consisting of reacting the polymer of formula (I) with the reagent $R_6$—Y, wherein Y is defined above, and $R_6$ is an aliphatic or arylaliphatic group defined above.

Further, in the situation where the starting diamine has the formula:

$$\begin{array}{c} R_1 \\ | \\ N-(CH_2)_n-N(R_5)-(CH_2)_n-N \\ | \\ R_2 \end{array} \begin{array}{c} R_3 \\ | \\ \\ | \\ R_4 \end{array}$$

it is possible to obtain a crosslinked polymer either by using an excess of the $B(X)_2$ reagent, and in this case a polymer of formula (I) will be obtained with $R_6-B$, or, after having reacted said starting amine with a fairly equimolecular amount of the $B(X)_2$ reagent, reacting the resulting polymer with a derivative of the formula $Y-R_6$, $R_6$ being a bivalent group different from B. For example, 0.1 to 3 moles of reagent $R_6(Y)_2$ are used. The resulting crosslinked polymer of formula (I) is isolated under conditions making it possible to eliminate the excess reagent $R_6(Y)_2$. Thus it is possible to obtain a whole variety of polymers of formula (I) having variable degrees of crosslinking.

Although the invention is not limited to use of polymers of formula I with a degree of polymerization varying in a particular range, it can be pointed out that the polymers of formula (I) that can be used according to the invention have a molecular weight generally between 1,000 and 50,000.

They are generally soluble in at least one of the three solvents consisting of water, ethanol or a water-ethanol mixture.

On evaporation of their solution it is possible to obtain films that exhibit a particularly good affinity for hair.

Unlike some cationic agents, the polymers of formula (I) are generally compatible with nonionic derivatives used in a standard way in the preparation of compositions in gel form.

As indicated above, the polymers of formula (I) have advantageous cosmetic properties that permit them to be used in preparing cosmetic compositions.

This invention also relates to cosmetic compositions comprising at least one polymer of formula (I). These cosmetic compositions generally include at least one adjuvant generally used in cosmetic compositions.

The cosmetic compositions of the invention comprise polymers of formula (I) either as the main active ingredient or as an additive.

It should be noted that the cosmetic compositions according to the invention are both ready-to-use compositions and concentrates that have to be diluted before use. The cosmetic compositions of the invention therefore are not limited to a particular range of concentration of the polymer of formula (I).

Generally, in the cosmetic compositions of the invention the concentration of polymers of formula (I) is between 0.01 and 15% by weight, particularly between 0.1 and 10% and preferably between 0.25 and 5%.

The polymers of formula (I) have particularly interesting cosmetic properties when they are applied to hair.

Thus, when they are applied to the hair, either alone or with other active substances during a treatment such as shampooing, dyeing, setting, blow-drying, permanent waving, etc., they improve notably the quality of the hair.

For example, they favor treatment and facilitate untangling of wet hair. Even in a strong concentration, they do not give wet hair a sticky feeling.

Unlike usual cationic agents, they do not make dry hair heavy and therefore facilitate bouffant hairdos. They give dry hair life and a glossy appearance. Untangling of dry hair is facilitated.

They effectively contribute to eliminating the defects of hair sensitized by treatments such as bleaching, permanents or dyeing. Actually, it is known that sensitized hair is often dry, dull and rough and difficult to untangle and set.

In particular the polymers of formula (I) offer a great advantage when they are used as post-treatment agents, particularly in the form of rinse compositions (rinse lotions called rinses, creams or gels), which are applied after bleaching, dyeing, permanent waving or shampooing.

The cosmetic compositions for the hair according to the invention generally comprise at least one adjuvant generally used in cosmetic compositions for the hair.

These cosmetic compositions for the hair can be in the form of an aqueous, alcohol or dilute alcohol solution (the alcohol being a lower alcohol such as ethanol or isopropanol), or in the form of emulsions (particularly creams or lotions) or gels, or again in spray form. They can also be packaged in the form of aerosols containing a propellant such as, for example, nitrogen, nitrous oxide or fluorocarbons of the Freon type.

The adjuvants generally present in the cosmetic compositions for the hair according to the invention are, for example, perfumes, dyes, preserving agents, sequestering agents, thickening agents, emulsifying agents, filters, peptizing agents, etc., or again cosmetic resins usually used in compositions for the hair.

The formula (I) polymers can be present in the cosmetic compositions for the hair according to the invention, either as an additive or as the main active ingredient, in setting lotions, treating compositions, hairdo lotions, hairdo creams and gels, or again as an additive in shampoo, hair setting, waving permanent, hair dyeing or bleaching compositions, restructuring lotions, antiseborrheic treatment lotions, or hair lacquers.

The cosmetic compositions for the hair according to the invention therefore particularly comprise:

(a) treating compositions comprising as the active ingredient at least one polymer of formula (I).

These treating compositions can be lotions, creams or gels.

The amount of the polymer of formula (I) in these treating compositions can vary from 0.1 to 10% by weight and particularly from 0.25 to 5%.

The lotions are aqueous or dilute alcohol solutions of the polymer of formula (I).

The pH of these lotions is close to neutral and can vary, for example, from 5 to 8. If necessary, the pH can be brought to the desired value by adding a pH modifier which is either an acid such as citric acid or a base, particularly an alkanolamine such as monoethanolamine or triethanolamine. Generally, these lotions contain a perfume and/or a dye intended to color said lotions and/or a preserving agent.

To treat hair with such a lotion, said lotion is applied to wet hair, allowed to act for 3 to 15 minutes, then the hair is rinsed.

Then, if desired, a standard hair setting is done.

The treating creams are made with a support formulated on the basis of soaps or fatty alcohols in the presence of emulsifiers. The soaps can be made from natural or synthetic fatty acids having 12-20 carbon atoms, such as lauric acid, myristic acid, palmitic acid, oleic acid, ricinoleic acid, stearic acid, isotearic acid and their mixtures, in concentrations between 10 and 30% and alkalizing agents, such as soda, potash, ammonia, monoethanolamine, triethanolamine and their mixtures.

Besides the polymer of formula (I) and the soap, these creams can contain adjuvants such as fatty amides or fatty alcohols.

Of the fatty amides, the following compounds in particular can be used: mono- or di-ethanolamides of acids derived from copra, lauric acid, oleic acid or stearic acid in concentrations between 0 and 15%.

Of the fatty alcohols there can be used in particular oleyl, lauryl, myristyl, cetyl, stearyl, isostearyl alcohols in concentrations between 0 and 25%.

The creams can also be formulated from natural or synthetic alcohols having 12-20 carbon atoms in admixture with emulsifiers. Of the fatty alcohols there can be cited, in particular, copra alcohol, myristyl alcohol, cetyl alcohol, stearyl alcohol and hydroxystearyl alcohol in concentrations between 0.5 and 25%.

The emulsifiers can be, for example, either nonionic emulsifiers such as oxyethylenated or polyglycerolated fatty alcohols, for example, oleyl alcohol polyoxyethylenated with 10 to 30 moles of ethylene oxide, stearyl alcohol oxyethylenated with 10-15 or 20 moles of ethyl oxide, oleyl alcohol polyglyerolated with 4 moles of glycerol and synthetic fatty alcohols having 9-15 carbon atoms polyoxyethylenated with 5 to 10 moles of ethylene oxide, these nonionic emulsifiers being present in an amount of 1 to 25% by weight, or ionic emulsifiers such as alkyl sulfates, oxyethylenated or not, such as sodium lauryl sulfate, ammonium lauryl sulfate, sodium cetyl stearyl sulfate, triethanolamine cetyl stearyl sulfate, monoethanolamine lauryl sulfate, sodium lauryl ether sulfate oxyethylenated with 2.2 moles of ethylene oxide, for example, and monoethanolamine lauryl ether sulfate oxyethylenated with 2.2 moles of ethylene oxide, for example, these latter emulsifiers being present in concentrations between 0.5 and 15% by weight.

The treating gels contain thickening agents such as sodium alginate or gum arabic or cellulose derivatives in the presence or not of a solvent. It is also possible to thicken the lotions by including therein polyethyleneglycols and stearates or distearates of polyethyleneglycols or phosphoric esters and amides.

The concentration of the thickener can vary from 0.5 to 30% and preferably from 0.5 to 15% by weight.

The solvents used can be lower aliphatic alcohols, glycols and their ethers. The concentration of these solvents varies between 2 and 20%.

As indicated above, the treating compositions defined above can be used particularly after bleaching, dyeing, a permanent or a shampoo. After a setting time of 3 to 30 minutes, during which the composition is allowed to act, the hair is rinsed;

(b) shampoos comprising at least one polymer of formula (I) and at least a cationic, nonionic, anionic or amphoteric detergent or mixtures thereof.

The cationic detergents are in particular long-chain quaternary ammoniums, alkylpyridinium salts, polyether fatty amines or imidazoline derivatives.

The nonionic detergents are particularly ethers of polyethoxylated, polypropoxylated or polyglycerolated fatty alcohols, ethers of polyethoxylated, polypropoxylated or polyglycerolated alkyl phenols, esters of polyethoxylated, polypropoxylated and polyglycerolated fatty acids and sorbitol and polyethoxylated or polyglycerolated fatty amides.

The anionic surfactants are particularly the following compounds and their mixture: alkaline salts, ammonium salts, amine salts or aminoalcohol salts of the following compounds:

alkylsulfates, alkylether sulfates, alkylamide sulfates and ethersulfates, alkylarylpolyethersulfates and monoglyceride sulfates, alkylsulfonates, alkyl amide sulfonates, alkylarylsulfonates and $\alpha$-olefin sulfonates, alkylsulfosuccinates, alkylethersulfosuccinates, alkylamide sulfosuccinates and alkylsulfosuccinamates, alkylsulfoacetates and alkylpolyglycerol carboxylates, alkylphosphates and alkyletherphosphates, alkylsarcosinates, alkylpolypeptidates, alkylamidopolypeptidates, alkylisethionates and alkyltaurates, the alkyl radical of all these compounds being a linear chain of 12 to 18 carbon atoms;

fatty acids such as oleic, ricinoleic, palmitic and stearic acids, acids of copra oil and hydrogenated copra oil, carboxylic acids of polyglycol ethers having the formula:

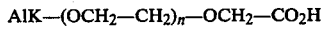

$$AlK-(OCH_2-CH_2)_n-OCH_2-CO_2H$$

where the AlK substitutent corresponds to a linear chain having 12 to 18 carbon atoms and where n is a whole number between 5 and 15.

The amphoteric surfactants are particularly alkylamino, mono- and dipropionates, betaines such as N-alkylbetaines, N-alkylsulfobetaines, N-alkylamidobetaines, cycloimidiniums such as alkylimidazolines, asparagine derivatives, the alkyl group in these surfactants designating a group having between 1 and 22 carbon atoms.

These compositions in shampoo form can also contain various adjuvants such as, for example, perfumes, dyes, preservatives, thickening agents, foam stabilizing agents and softening agents.

In these shampoos, the detergent concentration is generally between 3 and 50% by weight and the formula (I) polymer concentration is preferably between 0.1 and 5% and in particular between 0.25 and 5%;

(c) setting lotions or setting lotions in the form of blow-dry lotions, particularly for sensitized hair, characterized by the fact that they comprise at least one polymer of formula (I) in an aqueous, alcohol or dilute alcohol solution.

They can further contain at least another cosmetic resin. The cosmetic resins that can be used in such lotions are quite varied. They are known and described in cosmetology works. They are particularly homopolymers or copolymers, as for example, polyvinylpyrrolidone, copolymers of polyvinylpyrrolidone and vinyl acetate, copolymers of crotonic acid and vinyl acetate, etc.

The concentration of formula (I) polymers in these setting lotions varies particularly between 0.1 and 5%, for example, between 0.25 and 5%, and the cosmetic resin concentration varies approximately in the same proportions.

The pH of these setting lotions generally varies between 3 and 9 and preferably between 4.5 and 7.5;

(d) dye compositions for hair, characterized by the fact that they comprise at least one polymer of formula (I), at least a hair dyeing agent and a support.

The support is selected so as particularly to constitute a gel.

The concentration of formula (I) polymers in these dye compositions preferably varies between 0.5 and 15%.

In case of oxidation dyeing, the dye composition is packaged in two parts, put in a package comprising the mode of use, the second part being hydrogen peroxide. The two parts are mixed at the time of use.

The pH of these compositions is generally between 8 and 11 and can be adjusted by addition of a suitable alkalizing agent in the dye support, for example, by ammonia, monoethanolamine, diethanolamine or triethanolamine.

The dyes belong to the class of oxidation dyes to which can be added direct dyes such as the azoics, anthraquinones, nitro derivatives of the benzene series, indamines, indoanilines, indophenols, or other oxidation dyes such as leukoderivatives of these compounds.

Said oxidation dyes are aromatic compounds of the diamine, aminophenol or phenol type. These aromatic compounds are dye precursors that are transformed into dye compounds by condensation in the presence of a great excess of oxidant, generally, hydrogen peroxide. Of oxidation dyes there are distinguished, on the one hand, "bases" that are diamines or aminophenols (ortho or para derivatives) and, on the other hand, "modifiers" which are m-diamines, m-aminophenols, or polyphenols.

When the dye compositions are gelable liquids, they contain, besides the formula (I) polymer and dyes or dye precursors, either poyoxyethylenated or polyglycerolated nonionic derivatives, and solvents or liquid fatty acid soaps such as those of oleic or isostearic acid, and solvents. The soaps are soaps of soda, potash, ammonium or mono-, di- or tri-ethanolamine soaps;

(e) hair lacquers, wherein they comprise an alcohol or dilute alcohol solution of a usual cosmetic resin for lacquers, and at least one polymer of formula (I), this solution optionally being placed in an aerosol container and mixed with a propellant.

For example, it is possible to obtain an aerosol lacquer according to the invention by adding the usual cosmetic resin and the formula (I) polymer to the mixture of an anhydrous aliphatic alcohol such as ethanol or isopropanol and a propellant or a mixture of liquified propellants such as halogenated hydrocarbons of the trichlorofluoromethane or dichlorodifluoromethane type.

In these hair lacquer compositions the concentration of the cosmetic resin generally varies between 0.5 and 3% by weight, and the formula (I) polymer concentration generally varies between 0.1 and 5% and particularly between 0.25% and 3% by weight.

Of course, it is possible to add to these hair lacquers according to the invention adjuvants such as dyes, plasticizers or any other usual adjuvant;

(f) restructuring treating lotions comprising at least one agent having hair restructuring properties and at least one polymer of formula (I).

The restructuring agents that can be used in such lotions are, for example, the methylol derivatives described in French Pat. Nos. 1,519,979; 1,519,980; 1,519,981; 1,591,982 and 1,527,085.

In these lotions, the concentration of restructuring agent generally varies between 0.1 and 10% by weight, and the concentration of formula (I) polymer generally varies between 0.1 and 5% by weight;

(g) bleaching compositions that consist of supports in the form of powders, solutions, emulsions (including creams), gelable liquids containing at least a bleaching agent, for example, hydrogen peroxide, peroxides and solutions of persalts (persulfates, perborates, percarbonates).

Preferably, the bleaching compositions are supports in the form of creams or gelable liquids similar to those described above in connection with dye compositions. These supports are diluted at the time of use with a solution of hydrogen peroxide and/or peroxides.

They generally contain an alkalizing agent such as ammonia.

These bleaching compositions are applied by standard techniques;

(h) permanent wave compositions.

It is known that the standard technique for permanent deformation of hair consists, in a first stage, in making an opening of the S—S bonds of the keratin of the hair with a composition containing a reducing agent, then, preferably after the hair has been rinsed, in reconstituting said S—S bonds in a second stage by applying to the hair subjected to this reduction an oxidizing composition so as to give the hair the desired shape.

The formulation of said reducing and oxidizing compositions is known and described in works on cosmetology, particularly by E. Sidi and C. Zviak, "Problemes Capillaires," Paris, 1966 (Gauthier-Villard).

The permanent wave compositions of this application are particularly reducing compositions for the first stage of the permanent wave deformation operation.

Besides the reducing agent, these compositions contain adjuvants making it possible to offer them in the form of lotions or in powder form to be diluted in a liquid support.

The reducing agent for the first stage of the permanent wave operation is most often a mercaptan such as, for example, thioglycerol or again thioglycolic acid or its derivatives.

The oxidizing agent for the second stage of the permanent wave operation is, for example, hydrogen peroxide.

The concentration of the reducing agent is the concentration necessary to obtain the reduction of a sufficient number of S—S bonds. These concentrations are studied and described in works on cosmetology. For example, for thioglycolic acid the concentration is generally on the order of about 1 to 11%.

The pH of these compositions for the first stage of a permanent wave operation generally varies from 7 to 10.

The permanent wave compositions generally contain from 0.1 to 10% by weight of formula (I) polymer and particularly 0.25 to 5%.

The lotions for the first stage of the permanent wave operation most often are aqueous solutions that can further contain pH modifiers, auxiliary reducing agents such as sulfites, solvents such as ethanol or isopropanol, surfactants, perfumes and/or dyes.

The formula (I) polymers are compatible with the ingredients and adjuvants used in the permanent wave compositions.

The formula (I) polymers also exhibit interesting cosmetic properties when they are applied to the skin.

In particular, they give the skin a softness that is appreciable to the touch.

They further offer the advantage of being compatible with the ingredients used to make cosmetic skin compositions.

The cosmetic compositions according to the invention can be cosmetic skin compositions wherein they contain at least one polymer of formula (I).

Further, they generally comprise at least an active ingredient or adjuvant usually used in cosmetic skin compositions.

The cosmetic skin compositions according to the invention are provided, for example, in the form of emulsions (creams or lotions), gels, aqueous, alcohol or dilute alcohol solutions.

The concentration of formula (I) polymer in these skin compositions generally varies between 0.1 to 10% by weight.

The adjuvants generally present in these cosmetic compositions are, for example, perfumes, dyes, preservatives, thickeners, sequestering agents, emulsifiers, etc.

These skin compositions particularly constitute creams or lotions for treating the hands and face, antisolar creams, tinted creams, cleansing lotions, foaming liquids for baths, aftershave lotions, toilet waters, shaving foams, makeup pencils, colored or uncolored sticks, particularly for lips, for makeup or body hygiene, or again in deodorant compositions.

These compositions are prepared by usual methods.

Aftershave lotions or toilet waters are in the form of a dilute alcohol solution preferably containing a lower alcohol comprising 1 to 4 carbon atoms such as, preferably ethanol or isopropanol and comprising adjuvants usually used such as softening agents, cicatrizing agents, perfumes, etc.

When the composition is in the form of a shaving foam it generally contains soaps to which have optionally been added fatty acids, foam stabilizers, softeners such as glycerin, etc.

It can be packaged in an aerosol device in the presence of propellant gases by well known techniques.

The compositions of the invention can also be supports or bases in the form of an aqueous or dilute alcohol solution, cream, gel, dispersion or emulsion, and be employed in skin treatment cosmetic formulations.

The composition of the invention can also be used in treating nails and particularly constitute compositions for cleaning and polishing nails or as nail polishes. They contain at least one active ingredient and at least one adjuvant usually present in nail care compositions.

The formula (I) polymers can be present in cosmetic skin compositions according to the invention either as an additive or as the main active ingredient in hand and face treatment creams and lotions, or again as an additive in sun cream compositions, colored creams, cleansing lotions, foaming oil and liquid bath compositions.

This invention particularly relates to cosmetic compositions as defined above comprising at least any one of the polymers of formula (I) polymers described below in the experimental part.

The invention also has for its object a cosmetic treating process wherein a cosmetic composition containing at least one polymer of formula (I) as defined above, is applied to hair, skin or nails.

In particular, the invention has for its object a hair dyeing or bleaching process, principally characterized by the fact that there is applied to the hair a dyeing or bleaching composition as defined above, optionally containing dyes, and optionally mixed with an oxidizing agent such as hydrogen peroxide, the applied composition is allowed to act for a sufficient period to obtain the desired dyeing or bleaching effect, then the hair is rinsed.

Generally, the composition is allowed to act for 5 to 45 minutes, preferably for 15 to 30 minutes.

The amounts of dyeing or bleaching composition applied to the hair are generally between about 10 and 100 g.

According to another embodiment of the process of cosmetic treatment according to the invention, the invention also has for its object a process of permanent deformation of the hair wherein there is applied to the hair, optionally subjected to any extension, a sufficient amount of a reducing composition as defined above, it is allowed to act for about 5 to 20 minutes, then the hair is rinsed. There is then applied to the hair thus reduced an oxidizing composition in sufficient amount to reform the S-S bonds of the hair keratin, said reducing and/or oxidizing composition containing at least one polymer of formula (I).

The oxidizing agent is particularly hydrogen peroxide or a persalt.

Extension of the hair is generally effected by winding the hair on curlers, preferably, before application of the reducing composition.

After application of the oxidizing composition for a sufficient period, the extension of the hair is discontinued, then the hair is rinsed. It is possible to finish the operation by setting the hair.

According to another embodiment, the cosmetic treating process of this application is characterized by the fact that there is applied to the hair, particularly after dyeing, bleaching, permanently waving and shampooing the hair, a treating composition as defined above, this latter being allowed to act for about 3 to 15 minutes. Then the hair is rinsed.

The following examples illustrate the invention without, however, limiting it.

EXAMPLE 1

Preparation of a formula (I) polymer wherein

$R_1=R_2=R_3=R_4=CH_3$,

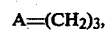
$A=(CH_2)_3$,

$B=CH_2CH_2-(OCH_2CH_2)_7OCH_2CH_2$ and

$X^\ominus = Cl^\ominus$.

The following mixture is heated for 8 hours with reflux and stirring: 43.7 g (0.1 mole) of $ClCH_2CH_2-(OCH_2CH_2)_7-OCH_2CH_2Cl$, hereinafter referred to as dichloride:

37 g of water and, 13.02 g (0.1 mole) of N,N,N',N',tetramethyl 1,3-propane diamine, 9.37 g of an aqueous, viscous solution of the polymer are obtained.

Analysis: ionic chlorine: 7.43%

Yield: 98.2%

EXAMPLE 2

Preparation of a formula (I) polymer wherein $R_1=R_2=R_3=R_4=CH_3$, $A=(CH_2)_{10}$, $B=CH_2CH_2-(OCH_2CH_2)_7OCH_2CH_2$ and $X^\ominus=Cl^\ominus$.

The following mixture is heated with reflux for 8 hours with stirring:
43.7 g (0.1 mole) of dichloride 1,
44 g of water and
22.84 g (0.1 mole) of N,N,N',N'-tetramethyl 1,10-decanediamine.
110.5 g of an aqueous viscous solution of the polymer of formula (I) having 6.20% of ionic chlorine are obtained.
Yield: 96.5%

EXAMPLE 3

Preparation of a formula (I) polymer wherein $R_1=R_2=R_3=R_4=CH_3$, $A=(CH_2)_6$, $B=CH_2CH_2-(OCH_2CH_2)_7OCH_2CH_2$ and $X^\ominus=Cl^\ominus$.

The following mixture is heated with reflux for 12 hours with stirring:
43.7 g (0.1 mole) of dichloride 1,
48.6 g of water and
22.40 g (0.1 mole) of N,N,N',N',-tetramethyl, 1,6-hexanediamine.
127.3 g of a viscous polymer solution having 6.94% ionic chlorine are obtained.
Yield: 96.2%

EXAMPLE 4

Preparation of a formula (I) polymer wherein $R_1=R_2=C_2H_5, R_3=R_4=CH_3$, $A=(CH_2)_3$, $B=CH_2CH_2-(OCH_2CH_2)_7OCH_2CH_2$, and $X^\ominus=Cl^\ominus$.

The following mixture is heated with reflux for 26 hours:
43.7 g (0.1 mole) of dichloride 1,
49.5 ml of water, and
28.86 g (0.1 mole) of N,N-diethyl N',N'-dimethyl, 1,3-propanediamine.
122.1 g of a clear viscous polymer solution having 5.81% ionic chlorine are obtained.

Yield: 100%.

EXAMPLE 5

Preparation of a formula (I) polymer wherein $R_1=R_3=CH_3, R_2=R_4=CH_2CH_2OH$, $A=(CH_2)_6$, $B=CH_2CH_2-(OCH_2CH_2)_7OCH_2CH_2$ and $X^\ominus=Cl^\ominus$.

The following mixture is heated for 49 hours with reflux (100° C.):
29.80 g (0.0682 mole) of dichloride 1,
31 g of water, and
15.85 g (0.0682 mole) of N,N'-dimethyl N,N'-dihydroxyethyl 1,6-hexanediamine.
76.7 of an aqueous polymer solution having 5.97% ionic chlorine are obtained.
Yield: 95%.

EXAMPLE 6

Preparation of a formula (I) polymer wherein $R_1=R_2=R_3=R_4=CH_3$, $A=(CH_2)_2$, $B=CH_2CH_2-(OCH_2CH_2)_7OCH_2CH_2$ and $X^\ominus=Cl^\ominus$.

The following mixture is heated with reflux for 18 hours with stirring:
65.55 g (0.15 mole) dichloride 1,
50 ml of water and
17.47 g (0.15 mole) of N,N,N',N'-1,2-tetramethyl ethanediamine.
133 g of a viscous polymer solution having 7.45% of ionic chlorine are obtained.
Yield: 93%.

EXAMPLE 7

Preparation of a formula (I) polymer wherein $R_1=R_3=CH_3, R_2=R_4=C_8H_{17}$, $A=(CH_2)_3$ $B=CH_2CH_2-(OCH_2CH_2)_7OCH_2CH_2$ and $X^\ominus=Cl^\ominus$.

The following mixture is heated for 120 hours with reflux:
43.7 g (0.1 mole) dichloride 1
45 g of water,
61 g of ethanol, and
32.7 g (0.1 mole) of N,N',-dimethyl N,N-di-n-octyl 1,3-propanediamine The solution is concentrated under vacuum. The polymer is washed 3 times with 250 ml of ethyl ether. The polymer is decanted and dried under vacuum at 70° C./0.1 mm Hg.
Weight obtained: 57.5 g,
% Cl⊖ 9%.
Yield: about 75%,
Appearance: gummy product.

EXAMPLE 8

Preparation of a formula (I) polymer wherein $R_1=R_2=R_3=R_4=CH_3$, $A=CH_2-CHOH-CH_2$, $B=CH_2CH_2+(OCH_2CH_2)_7OCH_2CH_2$ and $X^\ominus = Cl^\ominus$.

The following mixture is heated for 40 hours with reflux (100° C.) with stirring:
61.18 g (0.14 mole) of dichloride 1,
49 g of water and
20.46 g (0.14 mole) of N,N,N',N'-tetramethyl 1,3-diamino 2-propanol.
There are obtained 133 g of a viscous polymer solution having 7.34% of ionic chlorine.
Yield: 98.3%.

EXAMPLE 9

Preparation of a formula (i) polymer wherein $R_1=R_2=R_3=R_4=CH_3$, $A=(CH_2)_3$, $B=CH_2CH_2+(OCH_2CH_2)_{20}OCH_2CH_2$ and $X^\ominus = Cl^\ominus$.

The following mixture is heated with reflux for 13 hours with stirring: 77.77 g (0.075 mole) of dichloride 2,
58.4 g of water, and
9.77 g (0.075 mole) of N,N,N',N'-tetramethyl 1,3-propanediamine.
143.6 g of a viscous polymer solution having 3.66% of ionic chlorine are obtained.
Yield: 98.8%.
The dichloride 2 has the formula:

$ClCH_2CH_2-(OCH_2CH_2)_{20}OCH_2CH_2Cl$

EXAMPLE 10

Preparation of a formula (I) polymer with:

$R_1=R_2=R_3=R_4=CH_3$, $A=CH_2CHOHCH_2$, $B=CH_2CH_2+(OCH_2CH_2)_{20}OCH_2CH_2$ and $X^\ominus = Cl^\ominus$.

The following mixture is heated with reflux for 18 hours with stirring:
31.11 g (0.03 mole) of dichloride 2,
23.6 g of water, and
4.39 g (0.03 mole) of N,N,N',N'-tetramethyl 1,3-diamino 2-propanol.
59 g of a viscous polymer solution having 3.31% of ionic chlorine are obtained:
Yield: 92%

EXAMPLE 11

Preparation of a formula (I) polymer wherein $R_1=R_2=R_3=R_4=CH_3$, $A=(CH_2)_6$, $B=CH_2CH_2+(OCH_2CH_2)_{20}OCH_2CH_2$ and $X^\ominus = Cl^\ominus$.

The following mixture is heated with reflux (100° C.) for 12 hours with stirring:
25.92 g (0.035 mole) of dichloride 2,
20 ml of water, and
4.31 g (0.025 mole) N,N,N',N'-tetramethyl 1,6-hexanediamine.
48.85 g of a viscous polymer solution having 3.43% of ionic chlorine are obtained.
Yield: 94.6%

EXAMPLE 12

Preparation of a formula (I) polymer wherein $R_1=R_2=C_2H_5$, $R_3=R_4=CH_3$, $A=(CH_2)_3$ $B=CH_2CH_2+(OCH_2CH_2)_{20}OCH_2CH_2$ and $X^\ominus = Cl^\ominus$.

The following mixture is heated with reflux (100° C.) for 12 hours with stirring:
7.21 g (0.025 mole) of N,N-diethyl N',N'-dimethyl-1,3-propane diamine,
22 ml of water, and
25.92 g (0.025 mole) of dichloride 2
53.6 g of a viscous polymer solution having 3.29% of ionic chlorine are obtained.
Yield 100%.

EXAMPLE 13

Preparation of a formula (I) polymer wherein $R_1=R_2=R_3=R_4=CH_3$, $A=(CH_2)_2$, $B=CH_2CH_2+(OCH_2CH_2)_{20}OCH_2CH_2$ and $X^\ominus = Cl^\ominus$.

The following mixture is heated with reflux (100° C.) for 32 hours with stirring:
31.11 g (0.03 mole) of dichloride 2,
23 g of water, and
3.49 g (0.03 mole) of N,N,N',N'-tetramethyl-1,2-ethanediamine
57.6 g of a viscous polymer solution having 3.33% of ionic chlorine are obtained.
Yield: 90.3%

EXAMPLE 14

Preparation of a formula (I) polymer wherein $R_1=R_3=CH_3$, $R_2=R_4=C_4H_9$, $A=(CH_2)_6$, $B=CH_2CH_2-(OCH_2CH_2)_{77}OCH_2CH_2$ and $X^\ominus=Cl^\ominus$.

The following mixture is heated with reflux (100° C.) for 40 hours with stirring:
25.65 g (0.1 mole) N,N'-dimethyl N,N'-di-n-butyl 1,6-hexadiamine,
46.2 g of water, and
43.7 g (0.1 mole) of dichloride 1,
115 g of a viscous polymer solution having 6.01% of ionic chlorine are obtained.
Yield: 97.2%

7.85 g (0.06 mole) of N,N,N',N'-tetramethyl-1,3-propanediamine.

There is found 58% of ionic $Cl^\ominus$ (in relation to the % of theoretical ionic Cl). The resulting product is concentrated to dryness and then, dissolved several times with ethyl ether. It is dried and 25 g of the expected product having 10% $Cl^\ominus$ are obtained.
Yield=58%.

EXAMPLE 26

In the same way as in example 25 a formula (I) polymer is prepared wherein $R_1=R_2=R_3=R_4=CH_3$, $A=(CH_2)_3$, $B=-CH_2-CHOH-CH_2O-(CH_2CH_2O)_{13}CH_2-CHOH-CH_2-$ and $X^\ominus=Cl^\ominus$.

There are reacted for 130 hours with reflux 38.5 g (0.1 mole) of the dichloride, $ClCH_2-CHOH-CH_2-O-(CH_2CH_2O)_{13}CH_2-CHOH-CH_2-Cl$, in 120 ml of methanol with
13.02 g (0.1 mole) of N,N,N',N'-tetramethyl-1,3-propanediamine.

There is found 64.5% of ionic $Cl^\ominus$ (in relation to the

| Example No. | $R_1$ | $R_2$ | $R_3$ | $R_4$ | A | B | X |
|---|---|---|---|---|---|---|---|
| 15 | $CH_3$ | $CH_3$ | $CH_3$ | $CH_3$ | $-CH_2-CHOH-CH_2-$ | $-(CH_2-CH_2-O)_3-CH_2-CH_2$ | Cl |
| 16 | $CH_3$ | $CH_3$ | $CH_3$ | $CH_3$ | $-CH_2-CHOH-CH_2-$ | $-(CH_2-CH_2-O)_{12}-CH_2-CH_2$ | Cl |
| 17 | $CH_3$ | $CH_3$ | $CH_3$ | $CH_3$ | $-(CH_2)_3O-(CH_2)_4-O-(CH_2)_3-$ | $-(CH_2-CH_2-O)_7-CH_2-CH_2$ | Cl |
| 18 | $CH_3$ | $CH_3$ | $CH_3$ | $CH_3$ | $-(CH_2)_3-$ | $-(CH_2-CH_2-O)_2-CH_2-CH_2$ | Cl |
| 19 | $CH_3$ | $CH_3$ | $CH_3$ | $CH_3$ | $-(CH_2)_3-$ | $-(CH_2-CH_2-O)_3-CH_2-CH_2$ | Cl |
| 20 | $CH_3$ | $CH_3$ | $CH_3$ | $CH_3$ | $-(CH_2)_3-$ | $-(CH_2-CH_2-O)_5-CH_2-CH_2$ | Cl |
| 21 | $CH_3$ | $CH_3$ | $CH_3$ | $CH_3$ | $-(CH_2)_3-$ | $-(CH_2-CH_2-O)_{11}-CH_2-CH_2$ | Cl |
| 22 | $CH_3$ | $CH_3$ | $CH_3$ | $CH_3$ | $-CH_2-CH_2-O-CH_2-CH_2-$ | $-(CH_2)_3-O-(CH_2)_4-O-(CH_2)_3-$ | Cl |
| 23 | $CH_3$ | $CH_3$ | $CH_3$ | $CH_3$ | $-(CH_2)_3-$ | $-(CH_2)_4-O]_7-(CH_2)_4-$ | Cl |
| 24 | $CH_3$ | $CH_3$ | $CH_3$ | $CH_3$ | $-(CH_2)_6-$ | $-(CH_2)_3-O-(CH_2)_4-O-(CH_2)_3-$ | Cl |

EXAMPLE 25

Preparation of a formula (I) polymer wherein $R_1=R_2=R_3=R_4=CH_3$, $A=(CH_2)_3$, $B=-CH_2-CHOH-CH_2-O-(CH_2CH_2O)_8-CH_2CHOH-CH_2-$ and $X^\ominus=Cl^\ominus$.

There are heated for 130 hours with reflux 35.10 g (0.06 mole) of the following dichloride, $ClCH_2-CHOH-CH_2-O-(CH_2CH_2O)_8CH_2-CHOH-CH_2-Cl$, in 110 ml of methanol with theoretical $Cl^\ominus$). The resulting product is dissolved several times with ethyl ether.

There are obtained 33.2 g of product having 13.8% of $Cl^\ominus$.
Yield: 64.2%

EXAMPLES OF MAKING AND USE OF COSMETIC COMPOSITIONS

EXAMPLE A:

Ammonia oil for use as an oxidation hair dye:

| | |
|---|---|
| triethanolamine laurylsulfate with 40% active material | 2.5 g |
| 2-octyldodecanol marketed under the name EUTANOL by the HENKEL company | 7.5 g |
| oleic diethanolamide | 7.0 g |
| oleocetyl alcohol oxyethylenated with 30 moles of ethylene oxide, sold under the name of Mergital OC 30 by the HENKEL Co. | 3.0 g |
| oleic acid | 20.0 g |
| Polymer of Example 9 | 2.5 g |
| benzyl alcohol | 10 g |

-continued

| | |
|---|---|
| 96° ethyl alcohol | 10 g |
| ammonia at 22° Be | 18 ml |
| N,N—bis (2-hydroxyethyl)paraphenylene diamine | 1 g |
| p-aminophenol | 0.4 g |
| resorcin | 0.15 g |
| m-aminophenol | 0.1 g |
| alphanaphthol | 0.4 g |
| hydroquinone | 0.1 g |
| ethylenediaminetetraacetic acid | 0.24 g |
| sodium bisulfite (d = 1.32) | 1 ml |
| water sufficient for | 100 g |

There are mixed in a bowl 30 g of this support with 30 g of 20 volume hydrogen peroxide. A consistent gel is obtained that is pleasant to apply and adheres well to the hair. It is applied with a brush. It is allowed to stand for 30 to 40 minutes and is rinsed.

The hair untangles easily. The touch is silky. The hair is set and dried. The hair is glossy, lively, has body (volume), touch is silky and untangling is easy. A dark ash-blond shade is obtained.

EXAMPLE B:

Ammonia oil for use as an oxidation hair dye:

| | |
|---|---|
| 2-octyldodecaol sold under the name EUTANOL G by the HENKEL company | 12 g |
| oleic diethanolamide | 9 g |
| oleocetyl alcohol oxyethylenated with 30 moles ethylene oxide sold under the name of Mergital OC 30 by the HENKEL company | 2 g |
| oleic acid | 20 g |
| polymer of example 8 | 3 g |
| benzyl alcohol | 9 g |
| 96° ethyl alcohol | 9 g |
| ammonia at 22° Be | 17.5 ml |
| p-aminophenol | 0.30 g |
| resorcin | 0.65 g |
| m-aminophenol | 0.65 g |
| p-toluylene diamine | 0.15 g |
| ethylenediaminetetraacetic acid sold under Trilon B | 0.30 g |
| sodium bisulfite (d = 1.32) | 1.2 ml |
| water sufficient for | 100 g |

The operation is as in Example 1 and the same results are obtained except that a golden blond shade is obtained.

EXAMPLE C:

Ammonia oil for use as in oxidation hair dye.

| | |
|---|---|
| nonylphenol polyoxylthylenated with 9 moles of ethylene oxide | 3 g |
| oleyl alcohol | 9 g |
| oleic diethanolamide | 10 g |
| tallow amide hydrogenated with 50 moles of ethylene oxide | 2 g |
| oleic acid | 18 g |
| polymer of Example 6 | 2.5 g |
| 96° ethyl alcohol | 10 g |
| propyleneglycol | 10 g |
| monoethanolamine | 6.5 g |
| ammonia at 22° Be | 13 ml |
| 1-amino (2 methoxyethyl) 4-amino benzene dihydrochloride | 0.4 g |
| paraaminophenol | 0.25 g |
| resorcin | 0.07 g |
| m-aminophenol | 0.04 g |
| N (2-hydroxylethyl) 5-amino 2-methyl phenol | 0.12 g |
| 1-(2 hydroxyethyloxy) 2,4-diamino benzene dihydrochloride | 0.03 g |
| 1-methoxy 4-nitro β-4-hydroxyethylamino benzene | 0.07 g |
| 1-β-hydroxyethyloxy 3-nitro 4-amino benzene | 0.06 g |
| hydroquinone | 0.10 g |
| ethylenediaminetetraacetic acid sold under the name of Trilon B | 0.24 g |
| sodium bisulfite (d = 1.32) | 1 ml |
| water sufficient for | 100 g |

The operation is as in Example 1 and the same results are obtained except that a light blond shade is obtained.

EXAMPLE D:

Ammoniacal oil composition for lightening the hair.

| | |
|---|---|
| 2-octyldodecanol sold under the name of EUTANOL G by the HENKEL company | 8 g |
| triethanolamine laurylsulfate with 40% active material | 3 g |
| oleic diethanolamide | 6 g |
| tallow amide hydrogenated with 50 moles of ethylene oxide | 3.5 g |
| oleic acid | 18 g |
| polymer of Example 15 | 3 g |
| 96° ethyl alcohol | 15 g |
| propyleneglycol | 12 g |
| ammonia at 22° Be | 15 ml |
| ethylenediaminetetraacetic acid sold under the name of Trilon B | 0.3 g |
| water sufficient for | 100 g |

There are mixed in a bowl before use 40 g of this formula with 40 g of 30 volume hydrogen peroxide.

A gel is obtained that is pleasant to apply and adheres well to the hair. It is allowed to stand for 30 to 45 minutes and rinsed.

The wet hair easily untangles and its touch is silky. After drying, it is glossy, lively, has body (volume), its touch is silky and untangling is easy.

The hair is in a much better state than after bleaching with the same formula but without the cationic polymer. A dark blond coloration is obtained on dark brown hair after bleaching.

EXAMPLE E:

Shampoo composition

| | |
|---|---|
| polymer of Example 3 | 1.5 g |
| Na alkyl (C$_{12}$-C$_{14}$) ether sulfate (2.2 moles of ethylene oxide) with 25% active material | 20 g |
| ammonium chloride | 0.5 g |
| water sufficient for | 100 g |
| pH = 8 (NaOH) | |

EXAMPLE F:

Shampoo composition

| | |
|---|---|
| polymer of Example 4 | 0.7 g |
| triethanolamine salt of the product of condensation of copra acid and hydrolysate of animal protein at 40% (sold under the name of Maypon 4 CT by the STEPAN company) | 15.0 g |
| copra diethanolamide | 3 g |
| sodium chloride | 3 g |
| water sufficient for | 100 g |
| pH 7.4 (NaOH) | |

EXAMPLE G:

Shampoo composition

| | |
|---|---|
| polymer of Example 25 | 2 g |

| | |
|---|---|
| cycloimidazoline derivative of cocoanut oil with 38% active material sold under the name MIRANOL 2M conc. by the MIRANOL company | |
| 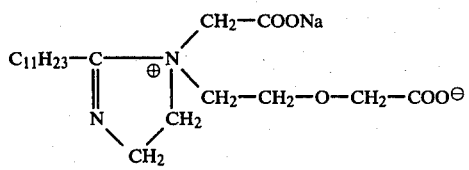 | 7 g |
| triethanolamine alkyl ($C_{12}C_{14}$)sulfate with 33% active material | 7 g |
| copra diethanolamide | 2 g |
| ammonium chloride | 1 g |
| water sufficient for | 100 g |
| pH 8.2 (NaOH) | |

EXAMPLE H:

Shampoo composition

| | |
|---|---|
| polymer of Example 5 | 2.5 g |
| MIRANOL C.2 M sold under the name MIRANOL C2M | 7 g |
| polyglycerolated fatty diglycolamide of the formula R—CO—NH—$CH_2$—$CH_2O(CH_2)_2$—[—O—$CH_2$—CHOH—$CH_2$]$_n$—OH wherein n has an average statistical value of 3.5 and R = amides of natural fatty acids of $C_{12}$ to $C_{18}$ | 5 g |
| sodium chloride | 3 g |
| copra diethanolamide | 3 g |
| water sufficient for | 100 g |
| pH = 7.3 (HCl) | |

EXAMPLE I:

Shampoo composition

| | |
|---|---|
| polymer of Example 11 | 0.15 g |
| sodium n-alkanesulfonate obtained by sulfoxidation of n-paraffin, sold under the name Hostapur SAS 30 by the HOECHST company | 12 g * |
| hydroxypropylmethyl cellulose, sold under the name Methocel F 4 M by the DOW company | 0.2 g * |
| copra diethanolamide | 3 g |
| water sufficient for | 100 g |
| pH = 5.9 (HCl) | |
| * = in active material | |

EXAMPLE J:

Hair rinse composition

| | |
|---|---|
| polymer of example 11 | 5 g * |
| cetyl alcohol | 7 g * |
| mixture of fatty alcohols and oxyethylenated products sold under the name of POLAWAX GP 200 by the CRODA (LTD) company, active material | 3 g |
| casein derivative sold under the name of HYDAGEN P by the HENKEL company in 50% solution | 2 g |
| tetradecyltrimethyl ammonium chloride | 0.5 g |
| water, dye (s) sufficient for | 100 g |
| pH = 7.6 (citric acid) | |
| * = in active material | |

We claim:

1. A cosmetic composition for application to the hair, skin or nails comprising in a cosmetic vehicle selected from the group consisting of water, a lower alkanol and a dilute lower alkanol solution, 0.01 to 15 percent by weight of said composition of a cationic polymer having units of the formula

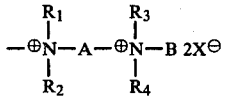

and having a molecular weight between 1,000 and 50,000, wherein $R_1$, $R_2$, $R_3$ and $R_4$ each independently represent alkyl or hydroxyalkyl, wherein the alkyl of each has 1-20 carbon atoms, A is alkylene, hydroxyalkylene, —($CH_2$)$_n$—Z—($CH_2$)$_n$— wherein Z is oxygen and n is a whole number ranging from 2 to 10, or —EO)$_{\overline{m1}}$(DO)$_{\overline{m}}$D wherein E represents alkylene or hydroxyalkylene containing 1-10 carbon atoms, D represents a bivalent hydrocarbon containing 1 to 5 carbon atoms, $m_1$ represents 0 or 1, m represents 1-600 with the proviso that m is greater than 1 when $m_1$=0, $D_1$ represents E when $m_1$=1, and $D_1$ represents D when $m_1$=0, B represents —(EO)$_{\overline{m1}}$(DO)$_{\overline{m}}$D$_1$, wherein E, D, $D_1$, m and $m_1$ are defined above, and $X^\ominus$ represents a halide anion.

2. The cosmetic composition of claim 1 wherein X is Cl.

3. The cosmetic composition of claim 1 wherein said cationic polymer is present in an amount ranging from 0.1 to 10 percent by weight of said composition.

4. The cosmetic composition of claim 1 wherein said cationic polymer is present in an amount ranging from 0.25 to 5 percent by weight of said composition.

5. The cosmetic composition of claim 1 wherein said lower alkanol is ethanol or isopropanol.

6. The cosmetic composition of claim 1 for treating the hair wherein said cosmetic vehicle is water or a dilute lower alkanol solution and said cationic polymer is present in an amount ranging from 0.1 to 10 percent by weight of said composition, said composition having a pH ranging from 5 to 8.

7. The cosmetic composition of claim 6 wherein the lower alkanol is ethanol or isopropanol.

8. The cosmetic composition of claim 6 which also includes a soap present in an amount between 10 and 30 percent by weight of said composition and a nonionic emulsifier present in an amount of 1 to 25 percent by weight of said composition.

9. The cosmetic composition of claim 6 which also includes a soap present in an amount between 10 and 30 percent by weight of said composition and an ionic emulsifier present in an amount between 0.5 and 15 percent by weight of said composition.

10. The cosmetic composition of claim 8 or 9 which also includes from 0 to 15 weight percent of mono- or di-ethanolamide of acids derived from copra, lauric acid, oleic acid or stearic acid.

11. The cosmetic composition of claim 8 or 9 which also includes from 0 to 25 weight percent of a fatty alcohol selected from the group consisting of oleyl, lauryl, myristyl, cetyl, stearyl and isostearyl alcohols.

12. The cosmetic composition of claim 6 which also includes a natural or synthetic alcohol having 12-18 carbon atoms present in an amount ranging from 0.5 to 25 percent by weight of said composition and a nonionic emulsifier present in an amount of 1 to 25 percent by weight of said composition.

13. The cosmetic composition of claim 6 which also includes a natural or synthetic alcohol having 12-18 carbon atoms present in an amount ranging from 0.5 to 25 percent by weight of said composition and an ionic emulsifier present in an amount of 0.5 to 15 percent by weight of said composition.

14. The cosmetic composition of claims 12 or 13 wherein said alcohol is copra alcohol, myristyl alcohol, cetyl alcohol, stearyl alcohol or hydroxystearyl alcohol.

15. The cosmetic composition of claim 6 which also contains from 0.5 to 30 percent by weight of a thickener, said thickener being sodium alginate, gum arabic, polyethylene glycol, polyethylene glycol stearate or polyethylene glycol distearate.

16. The cosmetic composition of claim 1 for use as a shampoo, wherein said cationic polymer is present in an amount ranging from 0.1 to 5 percent by weight of said composition, said composition also including from 3 to 50 percent by weight of a cationic, nonionic, anionic or amphoteric detergent, or a mixture thereof.

17. The cosmetic composition of claim 1 for use as a hair setting lotion, wherein said cationic polymer is present in an amount ranging from 0.1 to 5 percent by weight of said composition, said composition also including from 0.1 to 5 percent by weight of, as a cosmetic resin, polyvinyl pyrrolidone, a copolymer of polyvinyl pyrrolidone and vinyl acetate or a copolymer of crotonic acid and vinyl acetate, said composition having a pH ranging from 3 to 9.

18. The cosmetic composition of claim 1 for use as a hair dye composition which also includes a hair dyeing amount of a hair dye.

19. The cosmetic composition of claim 18 wherein the cationic polymer is present in an amount ranging from 0.5 to 15 percent by weight of said composition.

20. The cosmetic composition of claim 1 for use as a hair lacquer composition, said composition also including from 0.5 to 3 percent by weight of, as a cosmetic resin, polyvinyl pyrrolidone, a copolymer of polyvinyl pyrrolidone and vinyl acetate or a copolymer of crotonic acid and vinyl acetate, and an aerosol propellant, said cosmetic vehicle being a lower alkanol.

21. The cosmetic composition of claim 20 wherein the lower alkanol is ethanol or isopropanol.

22. The cosmetic composition of claim 1 for use as a hair restructuring lotion, said composition also containing a methylol derivative as a restructuring agent present in an amount ranging from 0.1 to 10 percent by weight of said composition and said cationic polymer being present in an amount ranging from 0.1 to 5 percent by weight of said composition.

23. The cosmetic composition of claim 1 for use as a hair bleaching composition, said composition also containing a hair bleaching agent in an amount effective to bleach the hair.

24. The cosmetic composition of claim 1 for use as a reducing composition for the first stage of a permanent waving operation, said composition also containing a reducing agent in an amount effective for opening the S—S bonds of the hair keratin, said composition having a pH ranging from 7 to 10, the said cationic polymer being present in an amount ranging from 0.1 to 10 percent by weight of said composition.

25. The cosmetic composition of claim 1 for use as an oxidizing composition for reconstituting the S—S bonds of hair keratin in a second stage of a permanent waving operation, said composition also containing an oxidizing agent in an amount effective to reconstitute the S—S bonds of the hair keratin, thereby giving the hair the desired shape, the said cationic polymer being present in an amount ranging from 0.1 to 10 percent by weight of said composition.

26. A process for treating the hair, skin or nails comprising applying thereto an effective amount of the cosmetic composition of claim 1.

27. A process for dyeing the hair comprising applying to the hair an effective amount of the hair dye composition of claim 18, permitting said composition to remain in contact with the hair for a time sufficient to dye said hair, and thereafter rinsing said hair.

28. The process of claim 27 wherein said hair dye composition is permitted to remain in contact with the hair for a period of time ranging from 5 to 45 minutes.

29. The process of claim 27 wherein between about 10 to 100 g of said hair dye composition are applied to the hair.

30. A process for bleaching the hair comprising applying to the hair an effective amount of the hair bleaching composition of claim 23, permitting said composition to remain in contact with the hair for a time sufficient to bleach said hair, and thereafter rinsing the hair.

31. The process of claim 30 wherein said hair bleaching composition is permitted to remain in contact with the hair for a period of time ranging from 5 to 45 minutes.

32. The process of claim 30 wherein between about 10 to 100 g of said hair bleaching composition are applied to the hair.

33. A process for reducing the S—S bonds of hair keratin in a first stage of a permanent waving operation comprising applying to the hair an effective amount of the reducing composition of claim 24 so as to reduce the S—S bonds of the hair keratin, permitting said composition to remain in contact with the hair for a period of time ranging from about 5 to 20 minutes and thereafter rinsing the hair.

34. A process for reconstituting the S—S bonds of hair keratin in a second stage of a permanent waving operation comprising applying to the hair an effective amount of the oxidizing composition of claim 25 for a time sufficient to reconstitute the S—S bonds of the hair keratin and thereafter rinsing the hair.

35. A process for treating the hair subsequent to bleaching, dyeing, permanently waving or shampooing the hair, comprising applying thereto the composition of claim 6, permitting said composition to remain in contact with the hair for a period of time ranging from about 3 to 15 minutes, and thereafter rinsing the hair.

36. A cosmetic composition for application to the hair, skin or nails comprising in a cosmetic vehicle selected from the group consisting of water, a lower alkanol and a dilute lower alkanol solution, 0.01 to 15 percent by weight of said composition of a cationic polymer having units of the formula

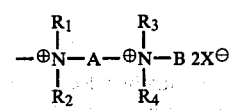

and having a molecular weight between 1,000 and 50,000, wherein $R_1$, $R_2$, $R_3$, $R_4$, A, B and X are selected from the combinations of (1) $R_1$, $R_2$, $R_3$ and $R_4$ each equal $CH_3$, $A=(CH_2)_3$, $B=CH_2CH_2+OCH_2CH_2)_{77}OCH_2CH_2$ and $X=Cl$;

(2) $R_1$, $R_2$, $R_3$ and $R_4$ each equal $CH_3$, $A=(CH_2)_{10}$, $B=CH_2CH_2+OCH_2CH_2)_7OCH_2CH_2$ and $X=Cl$;

(3) $R_1$, $R_2$, $R_3$ and $R_4$ each equal $CH_3$, $A=(CH_2)_6$, $B=CH_2CH_2+OCH_2CH_2)_{77}OCH_2CH_2$ and $X=Cl$;

(4) $R_1$ and $R_2=C_2H_5$, $R_3$ and $R_4=CH_3$, $A=(CH_2)_3$, $B=CH_2CH_2+OCH_2CH_2)_{77}OCH_2CH_2$ and $X=Cl$;

(5) $R_1$ and $R_3=CH_3$, $R_2$ and $R_4=C_2H_4OH$, $A=(CH_2)_6$, $B=CH_2-CH_2+OCH_2CH_2)_{77}OCH_2CH_2$ and $X=Cl$;

(6) $R_1$, $R_2$, $R_3$ and $R_4$ each equal $CH_3$, $A=(CH_2)_2$, $B=CH_2-CH_2+OCH_2CH_2)_{77}OCH_2CH_2$ and $X=Cl$;

(7) $R_1$ and $R_3=CH_3$, $R_2$ and $R_4=C_8H_{17}$, $A=(CH_2)_3$, $B=CH_2-CH_2+OCH_2CH_2)_{77}OCH_2CH_2$ and $X=Cl$;

(8) $R_1$, $R_2$, $R_3$ and $R_4$ each equal $CH_3$, $A=CH_2-CHOH-CH_2$, $B=CH_2-CH_2+OCH_2CH_2)_{77}OCH_2CH_2$ and $X=Cl$;

(9) $R_1$, $R_2$, $R_3$ and $R_4$ each equal $CH_3$, $A=(CH_2)_3$, $B=CH_2-CH_2+OCH_2CH_2)_{20}OCH_2+CH_2$ and $X=Cl$;

(10) $R_1$, $R_2$, $R_3$ and $R_4$ each equal $CH_3$, $A=CH_2-CHOH-CH_2$, $B=CH_2-CH_2+OCH_2CH_2)_{20}OCH_2-CH_2$ and $X=Cl$;

(11) $R_1$, $R_2$, $R_3$ and $R_4$ each equal $CH_3$, $A=(CH_2)_6$, $B=CH_2-CH_2+OCH_2CH_2)_{20}OCH_2CH_2$ and $X=Cl$;

(12) $R_1$ and $R_2=C_2H_5$, $R_3$ and $R_4=CH_3$, $A=(CH_2)_3$, $B=CH_2-CH_2+OCH_2CH_2)_{20}OCH_2CH_2$ and $X=Cl$;

(13) $R_1$, $R_3$, $R_3$ and $R_4$ each equal $CH_3$, $A=(CH_2)_2$, $B=CH_2-CH_2+OCH_2CH_2)_{20}OCH_2CH_2$ and $X=Cl$;

(14) $R_1$ and $R_3=CH_3$, $R_2$ and $R_4=C_4H_9$, $A=(CH_2)_6$, $B=CH_2CH_2+OCH_2CH_2)_{77}OCH_2CH_2$ and $X=Cl$;

(15) $R_1$, $R_2$, $R_3$ and $R_4$ each equal $CH_3$, $A=CH_2-CHOH-CH_2$, $B=-CH_2+CH_2O)_3CH_2CH_2$ and $X=Cl$;

(16) $R_1$, $R_2$, $R_3$ and $R_4$ each equal $CH_3$, $A=-CH_2-CHOH-CH_2$, $B=-CH_2CH_2+O)_{12}CH_2CH_2$ and $X=Cl$;

(17) $R_1$, $R_2$, $R_3$ and $R_4$ each equal $CH_3$, $A=+CH_2)_3-O-(CH_2)_4-O-(CH_2)_3$, $B=+CH_2CH_2O)_7CH_2CH_2$ and $X=Cl$;

(18) $R_1$, $R_2$, $R_3$ and $R_4$ each equal $CH_3$, $A=(CH_2)_3$, $B=+CH_2CH_2-O)_2CH_2CH_2$ and $X=Cl$;

(19) $R_1$, $R_2$, $R_3$ and $R_4$ each equal $CH_3$, $A=(CH_2)_3$, $B=+CH_2CH_2-O)_3CH_2CH_2$ and $X=Cl$;

(20) $R_1$, $R_2$, $R_3$ and $R_4$ each equal $CH_3$, $A=(CH_2)_3$, $B=+CH_2CH_2-O)_5CH_2CH_2$ and $X=Cl$;

(21) $R_1$, $R_2$, $R_3$ and $R_4$ each equal $CH_3$, $A=(CH_2)_3$, $B=+CH_2CH_2-O)_{11}CH_2CH_2$ and $X=Cl$;

(22) $R_1$, $R_2$, $R_3$ and $R_4$ each equal $CH_3$, $A=CH_2-CH_2-O-CH_2-CH_2$, $B=+CH_2)_3-O-(CH_2)_4-O-(CH_2)_3-$ and $X=Cl$;

(23) $R_1$, $R_2$, $R_3$ and $R_4$ each equal $CH_3$, $A=(CH_2)_3$, $B=+(CH_2)_4-O-)_7(CH_2)_4-$ and $X=Cl$;

(24) $R_1$, $R_2$, $R_3$ and $R_4$ each equal $CH_3$, $A=(CH_2)_6$, $B=+(CH_2)_3-O(CH_2)_4-O-(CH_2)_3$ and $X=Cl$;

(25) $R_1$, $R_2$, $R_3$ and $R_4$ each equal $CH_3$, $A=(CH_2)_3$, $B=CH_2-CHOH-CH_2-O+CH_2CH_2-O)_8CH_2-CHOH-CH_2$ and $X=Cl$; and

(26) $R_1$, $R_2$, $R_3$ and $R_4$ each equal $CH_3$, $A=(CH_2)_3$, $B=CH_2-CHOH-CH_2-O+CH_2CH_2-O)_3CH_2-CHOH-CH_2$, and $X=Cl$.

* * * * *